(12) United States Patent  
Falahee

(10) Patent No.: US 9,119,729 B2  
(45) Date of Patent: *Sep. 1, 2015

(54) STEERABLE INTERBODY FUSION CAGE

(71) Applicant: US SPINE, INC., Salt Lake City, UT (US)

(72) Inventor: Mark H. Falahee, Ann Arbor, MI (US)

(73) Assignee: US Spine, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/318,280

(22) Filed: Jun. 27, 2014

(65) Prior Publication Data

US 2014/0309743 A1 Oct. 16, 2014

Related U.S. Application Data

(63) Continuation of application No. 11/532,731, filed on Sep. 18, 2006, now Pat. No. 8,882,841.

(60) Provisional application No. 60/718,063, filed on Sep. 16, 2005.

(51) Int. Cl.
```
A61F 2/44      (2006.01)
A61F 2/28      (2006.01)
A61F 2/30      (2006.01)
A61F 2/46      (2006.01)
```

(52) U.S. Cl.  
CPC ............. *A61F 2/4455* (2013.01); *A61F 2/4611* (2013.01); *A61F 2002/2835* (2013.01); *A61F 2002/3082* (2013.01); *A61F 2002/30092* (2013.01); *A61F 2002/30112* (2013.01); *A61F 2002/30133* (2013.01); *A61F 2002/30471* (2013.01); *A61F 2002/30565* (2013.01); *A61F 2002/4415* (2013.01); *A61F 2002/4629* (2013.01); *A61F 2210/0014* (2013.01); *A61F 2220/0091* (2013.01); *A61F 2230/0004* (2013.01); *A61F 2230/0015* (2013.01)

(58) Field of Classification Search  
CPC ........................................ A61F 2/4465  
USPC ......................................... 623/17.11–17.16  
See application file for complete search history.

(56) References Cited

U.S. PATENT DOCUMENTS

| 6,387,130 | B1 * | 5/2002 | Stone et al. | 623/17.16 |
| 2006/0142858 | A1 * | 6/2006 | Colleran et al. | 623/17.11 |
| 2006/0247781 | A1 * | 11/2006 | Francis | 623/17.16 |

\* cited by examiner

*Primary Examiner* — Matthew Lawson  
(74) *Attorney, Agent, or Firm* — Phillips Ryther & Winchester; Matthew D. Thayne

(57) ABSTRACT

Intervertebral spacers, such as interbody vertebral cages, that facilitate minimally-invasive corrective restoration surgeries, and related methods. In some implementations, an introducer may be used introduce an intervertebral spacer in a first, straightened shape into an intervertebral disc space. The introducer may engage a plurality of adjacent recesses of the intervertebral spacer to maintain the intervertebral spacer in the first, straightened shape during introduction. An introducer, in some cases the same introducer, may be used to articulate the intervertebral spacer by actuating at least one hinge of the intervertebral spacer such that the intervertebral spacer assumes a second, curved shape once within the intervertebral disc space.

25 Claims, 2 Drawing Sheets

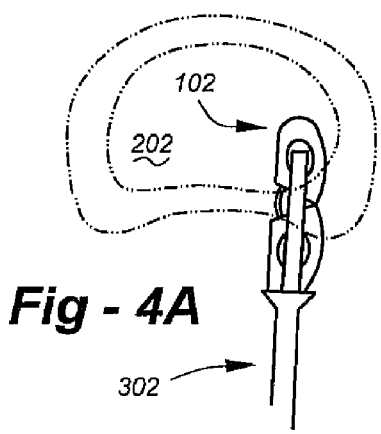
Fig - 4A
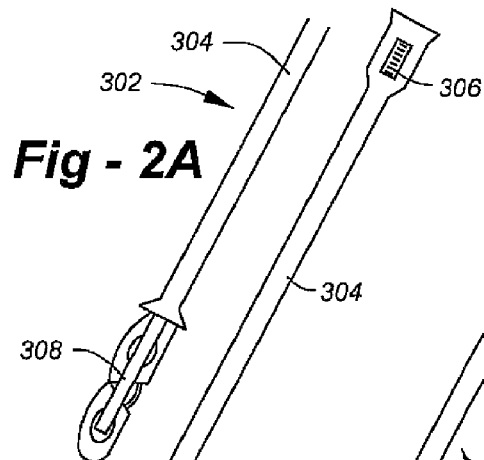
Fig - 2A
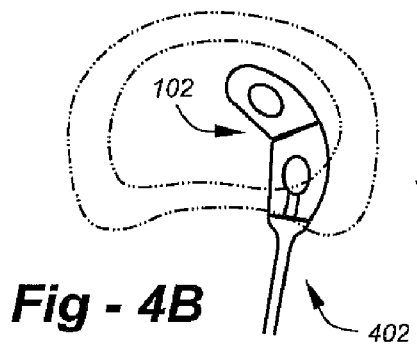
Fig - 4B
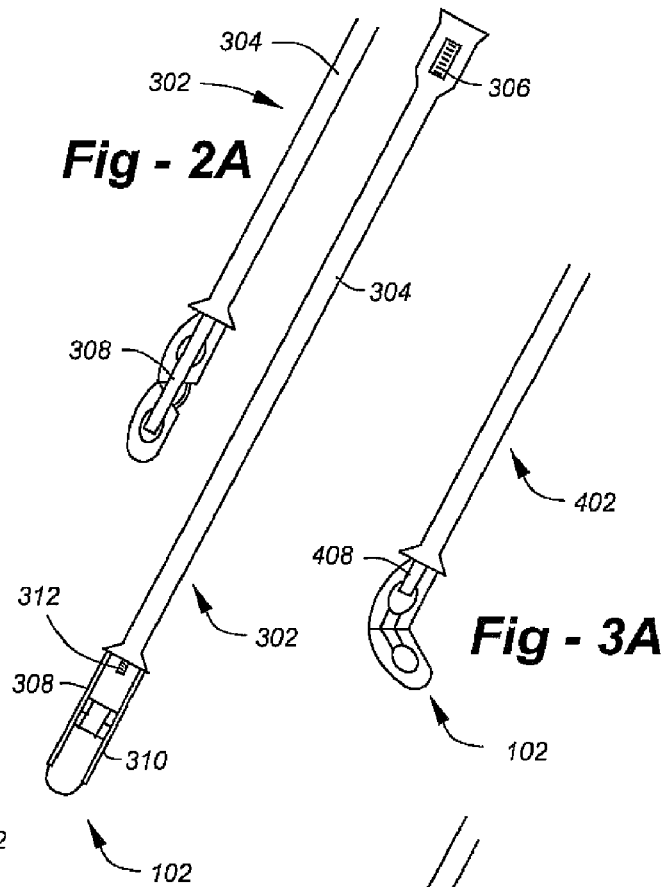
Fig - 2B
Fig - 3A
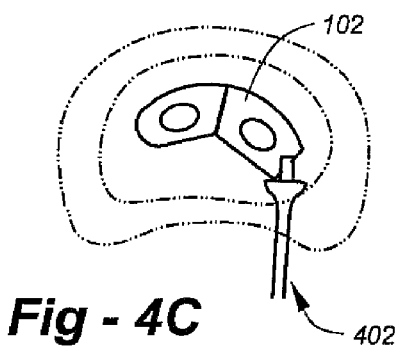
Fig - 4C
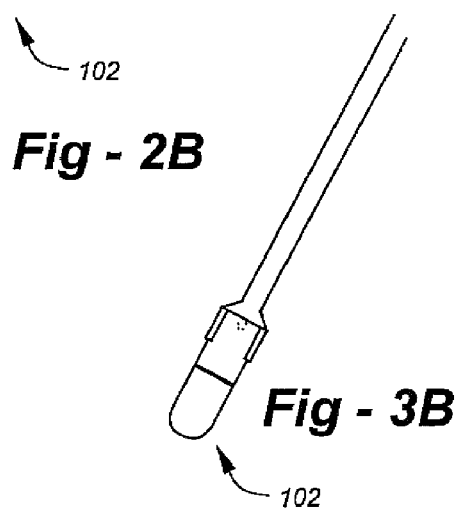
Fig - 3B

STEERABLE INTERBODY FUSION CAGE

CROSS-REFERENCE TO RELATED APPLICATIONS

This is a continuation application of U.S. patent application Ser. No. 11/532,731, filed on Sep. 18, 2006, and titled "STEERABLE INTERBODY FUSION CAGE," which claims the benefit of U.S. Provisional Patent Application No. 60/718,063, filed on Sep. 16, 2005, and also titled "STEERABLE INTERBODY FUSION CAGE." Both of the aforementioned applications are incorporated by reference herein in their entireties.

FIELD OF THE INVENTION

This invention relates generally to intervertebral cages and, in particular, to a steerable interbody fusion cage applicable to minimally invasive surgical (rviTS) procedures.

BACKGROUND OF THE INVENTION

One of the most common causes of chronic back pain is degenerative disc disease. The degeneration may start after a particular injury, or many occur due to multiple injuries over time. Degeneration usually takes several years. As the vertebrae grow closer, the openings in the back of the spine where the nerve roots leave the spinal canal become narrower. This can lead to pinching and irritation on the nerves, causing pain.

There are many surgical approaches and methods used to fuse the spine. Most involve the placement of a bone graft between the vertebrae. Supplemental hardware, such as plates, screws and cages may or may not be used, depending upon the indication.

An early cage design is described in U.S. Pat. No. 4,501,269 to Bagby, entitled "PROCESS FOR FUSING BONE JOINTS." According to the method, a hole is bored transversely across the joint and a slightly larger cylindrical basket is driven into the hole, thereby spreading the bones in resistance to the tensile forces of the surrounding tissue. Immediate stabilization of the joint is achieved by the implantation of the rigid cylindrical basket. Subsequent bone-to-bone fusion is achieved, both through and about the basket, which is filled with bone fragments produced during the boring step.

The Bagby patent states that the process is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint.

This stand-alone interbody fusion technique continued to evolve with material changes and the design of threaded cages to increase stability and decrease displacement rates. Bilateral, parallel implants were designed for use in the lumbar spine, with the first human implantation occurring in the early 1990s. The cylindrical titanium cages were threaded to screw into the endplates, thereby stabilizing the device and allowing for increased fusion rate with a stand-alone anterior device.

Ray and colleagues developed a similar titanium interbody fusion device which was initially used in posterior lumbar interbody fusions (PLIF), but expanded to include ALIF procedures (anterior lumbar interbody fusions). In 1985, Otero-Vich reported using threaded bone dowels for anterior cervical arthrodesis, and femoral ring allograft bone has subsequently been fashioned into cylindrical threaded dowels for lumbar application.

Currently, there are a wide number of available interbody fusion devices of varying design and material, including:
1) Cylindrical threaded titanium interbody cages;
2) Cylindrical threaded cortical bone dowels; and
3) Vertical interbody rings, boxes and wedges.

A typical intervertebral fusion cage is a large, hollow cylinder made of some type of metal, usually titanium. It is designed as a "cage" so that bone graft can be placed inside the hollow cylinder. Holes throughout the cage allow bone to form around and through the cage to allow a spinal fusion to occur between two vertebrae. Many of the newer types of intervertebral fusion cages are also designed to facilitate an open incision or a laparoscopic procedure.

An intervertebral fusion cage serves a couple important purposes. First, it distracts the vertebrae, making more room for the nerves, thereby decreasing pinching and irritation. The strong ligaments that surround the disc are also tightened, which decreases the segmental instability between the two vertebrae and decreases the mechanical pain in the spine. The cage also holds the two vertebrae in the correct position until a fusion occurs.

There are several drawbacks with existing approaches and techniques, such that further research and improved designs are desirable. Increased morbidity of anterior in-situ cage placement is not justified when less anatomic correction of the disc space is possible. Additionally, current PLIF and transverse lumbar interbody fusions (TLIF) cage and allograft placements require large dissections for exposure. PLIF and TLIF approaches also weaken existing posterior elements via bony destruction resulting from the operative procedure used to access the disc space.

SUMMARY OF THE INVENTION

This invention relates to interbody cages designed to facilitate minimally invasive approaches to the intervertebral disc for corrective restoration of disc height, stabilization between vertebra, and fusion. Cages according to the invention allow for a direct, minimally invasive, Posterior Lumbar Interbody Approach (PLIF) with preservation of the pars interarticularis and inferior facet of the superior vertebra. These bone elements are frequently sacrificed in the typical PLIF and TLIF approaches now in use with conventional designed cages.

The preferred embodiment provides a streamlined, slender straight contour with a central hinge or other articulating apparatus that allows the introduction of the cage into the operative field and disc space in a minimally invasive, bone-sparing manner. After partial insertion, the hinge component is activated, allowing the operator to steer the cage anterior-medially within the disc space to an anterior-central position within the intervertebral space. In this state the cage is shaped like a crescent, chevron or boomerang.

DESCRIPTION OF THE DRAWINGS

FIG. 2A is a top-down view showing a long-armed introducer for insertion of the cage in a straightened condition;

FIG. 2B is a side-view drawing of the long-armed introducer;

FIG. 3A is a top-down view showing a short-armed introducer for steering the cage through a curved path;

FIG. 3B is a side-view drawing of the short-armed introducer;

FIG. 4A is a drawing showing an initial stage of cage insertion using the long-armed introducer instrument;

FIG. 4B is a drawing showing an intermediate stage of cage insertion through a curved path; and FIG. 4C is a drawing showing a final stage of cage insertion oriented in this case to anterior center of an intervertebral disc space.

DETAILED DESCRIPTION OF THE INVENTION

Figure 1A:
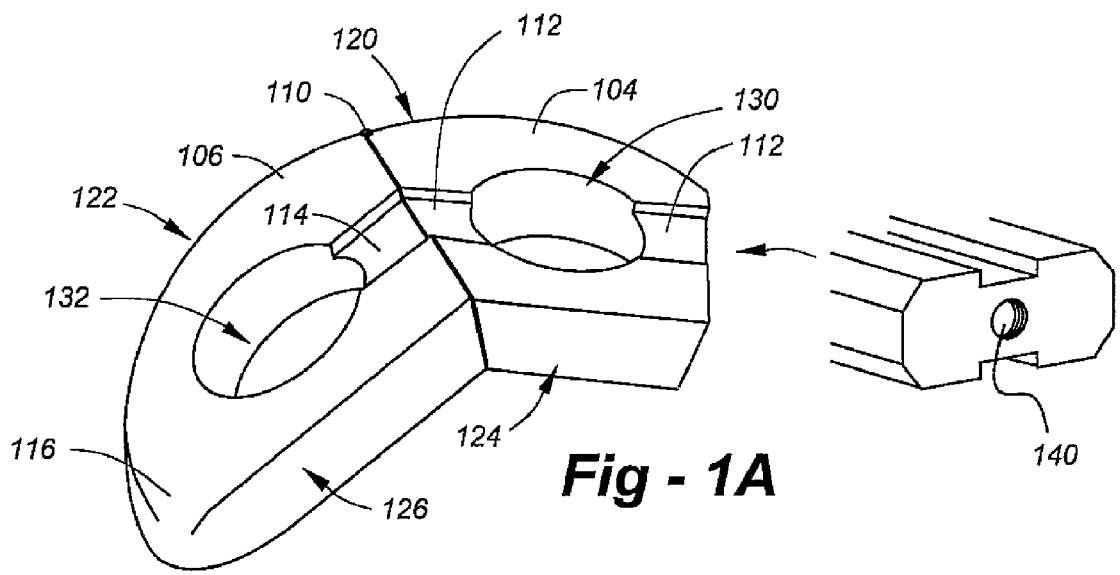
FIG. 1A is an oblique view of the preferred embodiment of the invention in a folded condition.

Making reference to the drawings, FIG. 1A is an oblique view of the preferred embodiment of the invention in a folded condition depicted generally at 102. The implant comprises a proximal portion 104 and a distal portion 106 joined by a hinge 110. Both portions include voids 130, 132 facilitating the introduction of bone graft and other biologic and or therapeutic substances. The proximal portion 104 includes a longitudinal recess 112, and the distal portion 106 includes a longitudinal recess 114. As shown in the end-view drawing at the right of FIG. 1A, these recesses are provided on the upper and lower surfaces of each portion. The end-view drawing also shows a central threaded hole 140 used for initial introduction.

In the preferred embodiment, the 'outer' surfaces 120, 122 of the respective portions 104, 106 are curved such that in the folded state of FIG. 1A a continuous outer surface is established. Although this is not necessary to the invention, curved surfaces better facilitate travel along a curved path as discussed in further detail below. The 'inner surfaces 124, 126 are preferably straight but may be curved as well. The distal portion preferably terminates in a smooth, blunt termination 116.

Figure 1B:
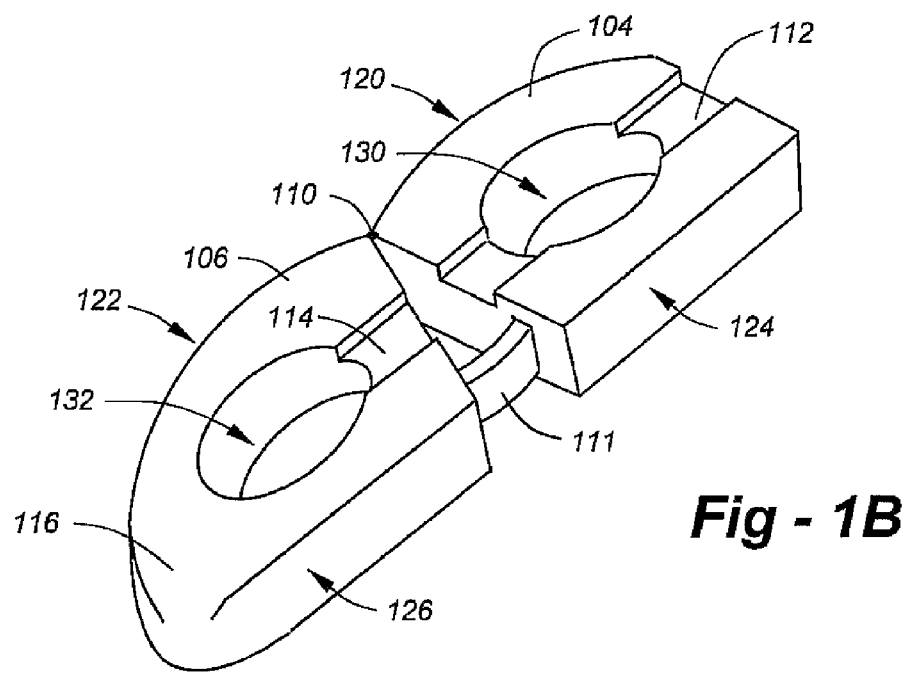
FIG. 1B is an oblique view of the preferred embodiment of the invention in an unfolded or straightened condition.

In the folded condition of FIG. 1A, recesses 112 and 114 on proximal and distal portions are not aligned, but rather form an angle. In the preferred embodiment in the folded condition the axes of the proximal and distal portions form an angle on the order of 40 degrees to optimize anterior medial positioning as described herein below. However, in the straightened condition of FIG. 1B, the recesses are aligned. FIG. 1B also shows the optional addition of a member 111 that stabilizes the hinging action while ensuring that the proximal and medial portions do not over-articulate.

FIG. 2A is a top-down view showing a long-armed introducer 302 used for inserting the cage in the straightened condition of FIG. 1B. The instrument includes a shaft 304 and a long arm 308 that fits into the recesses 112 and 114 of the proximal and distal portions, respectively. A bottom long arm 310 configured to fit into the bottom recesses of the proximal and portions as shown in FIG. 1A. At the proximal end of the long-armed introducer 302 is a thumbwheel to turn screw 312 to engage and disengage threads 140 shown in FIG. 1A. FIG. 2B is a side-view drawing of the long-armed introducer.

FIG. 3A is a top-down view showing a short-armed introducer 402 for steering the cage 102 through a curved path, and FIG. 3B is a side-view drawing of the short-armed introducer. This instrument has short arms such as 408 which engage only with the proximal portion of the cage, thereby facilitating articulation.

FIG. 4A is a drawing showing an initial stage of cage insertion using the long-armed introducer instrument 302. At this stage the cage 102 has just entered intradiscal space 202. FIG. 4B is a drawing showing an intermediate stage of cage insertion. Note that the long-armed introducer instrument 302 has been replaced with the short-armed introducer instrument 402, allowing travel through a curved path. FIG. 4C is a drawing showing a final stage of cage insertion oriented in this case to anterior center of an intervertebral disc space.

As an alternative to the final position shown in FIG. 4C, the cage may be left in the straight or open position for one-sided fixation. In the preferred embodiment, the cage is mirror-image symmetrical such that it may be flipped over and used for introduction into the other side of the body, regardless of whether straight or curved trajectory is deployed. The slender profile of the cage allows for bone and or osteoinductive/conductive materials to be placed within its walls, with additional room posterior to the cage for further grafting. The cage can be constructed of any biologically compatible material, including PEEK, PEK, carbon fiber, or other materials, radiolucent or otherwise.

In the preferred embodiment, the shape of cage anteriorly is contoured much like a rounded or bullet shape to facilitate anterior-central penetration. The posterior "docking portion" of the cage is flat to accommodate the introduction and driving tools and provides a stable surface for impact. Removal of the cage may be done via reversal of the insertion steps. Although only a single "hinge" is depicted, multiple points of articulation may be used, much like train cars that turn a corner. In addition, although the cage may bend and steer on its own, more active mechanisms such as springs and/or shape-memory materials may be used.

The invention claimed is:

1. A method of fusing vertebrae, comprising the steps of:
   providing a steerable intervertebral cage comprising:
      a distal portion having front, back, top, bottom, inner and outer surfaces;
      a proximal portion having front, back, top, bottom, inner and outer surfaces, and
      a hinge joining the front of the proximal portion to the back of the distal portion, such that the cage has a first, straightened shape with the hinge open and a second, crescent shape with the hinge closed, wherein the inner and outer surfaces of the distal and proximal portions define opposing surfaces of the crescent shape, wherein, in the second, crescent shape, the inner surface of the distal portion extends at an angle with respect to the inner surface of the proximal portion to form a "V" shape, wherein the inner surfaces of the distal and proximal portions of the intervertebral spacer are contiguous in the second, crescent shape, and wherein the inner surfaces of the distal and proximal portions of the intervertebral spacer are laterally spaced apart from one another in the first, straightened shape;
   introducing the cage in the first, straightened shape into an anterior central position within an intervertebral disc space using a posterior lumbar interbody fusion (PLIF) or transverse lumbar interbody fusion (TLIF) approach; and steering or allowing the cage to assume the second, crescent shape once within the intervertebral disc space.

2. The method of claim 1, further comprising using a first instrument to introduce the cage in the straightened shape into the anterior central position within the intervertebral disc space.

3. The method of claim 2, further comprising using a second instrument to steer or allow the cage to assume the second, crescent shape once within the intervertebral disc space, wherein the second instrument is distinct from the first instrument.

4. The method of claim 1, further comprising stabilizing a hinging action of the hinge of the steerable intervertebral cage using a stabilizing member.

5. The method of claim 4, wherein the stabilizing member extends between the distal portion and the proximal portion.

6. The method of claim 1, wherein the steerable intervertebral cage is configured such that, with the hinge open in the first, straightened shape, the inner surfaces of the proximal and distal portions of the steerable intervertebral cage are at least substantially coplanar to collectively define an inner surface of the steerable intervertebral cage opposite from an outer surface of the steerable intervertebral cage.

7. A method of fusing vertebrae, comprising the steps of:
providing a steerable intervertebral cage comprising:
a distal portion having front, back, top, bottom, inner and outer surfaces;
a proximal portion having front, back, top, bottom, inner and outer surfaces, and
at least one hinge configured to allow the cage to assume a first, straightened shape and configured to activate to allow the cage to assume a second, curved shape, wherein the inner surfaces of the distal portion and the proximal portion collectively define at least part of an inner surface of the steerable intervertebral cage in both the first, straightened shape and the second, curved shape, and wherein the inner surfaces of the distal and proximal portions are at least substantially coplanar when the steerable intervertebral cage is in the first, straightened shape;
introducing the cage in the first, straightened shape into an anterior central position within an intervertebral disc space; and
articulating the cage such that the cage assumes the second, curved shape once within the intervertebral disc space.

8. The method of claim 7, wherein the at least one hinge couples the front surface of the proximal portion to the back surface of the distal portion.

9. The method of claim 7, wherein the at least one hinge comprises a plurality of hinges.

10. The method of claim 7, wherein the curved shape comprises a crescent shape.

11. The method of claim 7, wherein the outer surfaces of the distal portion and the proximal portion form a continuous, convex curve in the second, curved shape.

12. The method of claim 7, wherein the inner surfaces of the proximal and distal portions are straight such that, with the at least one hinge closed in the second, curved shape the inner surfaces form a "V" shape, and such that, with the at least one hinge open in the first, straightened shape the straight inner surfaces are at least substantially contiguous and at least substantially coplanar.

13. The method of claim 7, wherein inner and outer surfaces of the distal and proximal portions define opposing surfaces of the curved shape.

14. The method of claim 13, wherein, in the curved shape, the inner surface of the distal portion extends at an angle with respect to the inner surface of the proximal portion to form a "V" shape.

15. The method of claim 14, wherein the inner surfaces of the distal and proximal portions are contiguous in the curved shape, and wherein the inner surfaces of the distal and proximal portions are spaced apart from one another in the straightened shape.

16. A method of fusing vertebrae, comprising the steps of:
using an introducer to introduce an intervertebral spacer in a first, straightened shape into an intervertebral disc space, wherein the introducer engages a plurality of adjacent recesses of the intervertebral spacer to maintain the intervertebral spacer in the first, straightened shape during introduction of the intervertebral spacer into the intervertebral disc space;
using an introducer to articulate the intervertebral spacer by actuating at least one hinge of the intervertebral spacer such that the intervertebral spacer assumes a second, curved shape once within the intervertebral disc space; and
positioning the intervertebral spacer in an anterior central position within the intervertebral disc space.

17. The method of claim 16, wherein the introducer used to introduce the intervertebral spacer in the first, straightened shape is distinct from the introducer used to articulate the intervertebral spacer by actuating at least one hinge of the intervertebral spacer.

18. The method of claim 17, wherein the introducer used to introduce the intervertebral spacer in the first, straightened shape comprises a long-armed introducer, and wherein the introducer used to articulate the intervertebral spacer comprises a short-armed introducer.

19. The method of claim 18, wherein the long-armed introducer comprises a long arm configured to engage each of the plurality of adjacent recesses of the intervertebral spacer to maintain the intervertebral spacer in the first, straightened shape.

20. The method of claim 19, wherein the short-armed introducer comprises a short arm having a length less than the long arm, wherein the short-armed introducer is configured to engage less than each of the plurality of adjacent recesses of the intervertebral spacer to allow the intervertebral spacer to articulate by actuating the at least one hinge of the intervertebral spacer.

21. The method of claim 16, wherein the intervertebral spacer comprises a distal portion and a proximal portion, wherein the at least one hinge couples the distal portion with the proximal portion.

22. The method of claim 21, wherein the proximal portion of the intervertebral spacer forms an angle with respect to the distal portion of the intervertebral spacer that is on the order of 40 degrees when the steerable intervertebral cage is in the first, straightened shape.

23. The method of claim 21, wherein outer surfaces of the distal portion and the proximal portion form a continuous, convex curve in the second, curved shape.

24. The method of claim 16, wherein the intervertebral spacer is configured such that, with the at least one hinge closed in the second, curved shape, inner surfaces of at least two portions of the intervertebral spacer form a "V" shape, and such that, with the at least one hinge open in the first, straightened shape, the inner surfaces of the at least two portions are at least substantially coplanar.

25. The method of claim 24, wherein the inner surfaces of the at least two portions of the intervertebral spacer are contiguous in the second, curved shape, and wherein the inner surfaces of the at least two portions of the intervertebral spacer are spaced apart from one another in the first, straightened shape.

* * * * *